United States Patent [19]

Doppelt

[11] Patent Number: 4,798,213
[45] Date of Patent: Jan. 17, 1989

[54] BONE BIOPSY APPARATUS

[76] Inventor: Samuel H. Doppelt, 18 Wadsworth Rd., Sudbury, Mass. 01776

[21] Appl. No.: 94,503

[22] Filed: Sep. 9, 1987

[51] Int. Cl.⁴ ............................................. A61B 10/00
[52] U.S. Cl. .................................... 128/754; 128/310; 604/264; 408/204; 408/703; 30/174; 30/278; 30/301
[58] Field of Search .......... 128/749, 751, 754, 303 B, 128/310; 604/93, 117, 158, 160, 161, 181, 264, 272; 30/278, 279, 286, 301, 316, 388, 173, 174; 408/204, 226–229, 231, DIG. 703

[56] References Cited

U.S. PATENT DOCUMENTS 3,628,524 12/1971 Jamshidi .............................. 128/754
4,142,517 3/1979 Stavropoulos et al. ............ 128/310
4,461,305 7/1984 Cibley ................................. 128/754

Primary Examiner—Edward M. Coven
Assistant Examiner—Randy Citrin
Attorney, Agent, or Firm—Blodgett & Blodgett

[57] ABSTRACT

Apparatus for obtaining a bone biopsy comprising a trocar which includes a guide tube with gripping teeth at one end and a tubular drill which is insertable through the tube. The drill has cutting teeth at its forward end and comprises an outer retaining sheath and an inner retaining sheath which is slidable axially within the outer retaining sheath. The inner retaining sheath consists of two separable longitudinal halves which separate when the inner retaining sheath is removed from the outer retaining sheath by means of an elongated extractor.

20 Claims, 4 Drawing Sheets

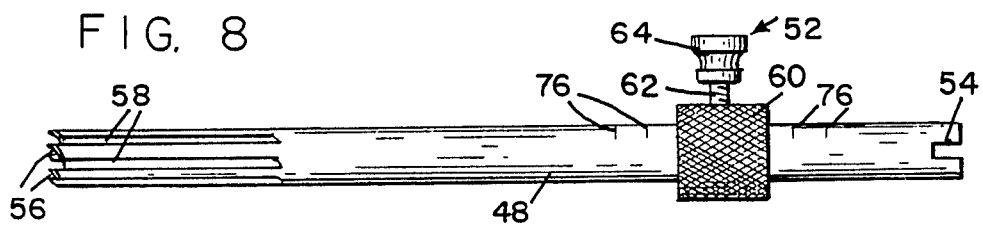
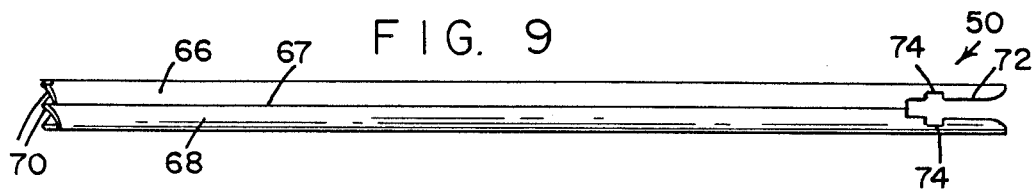
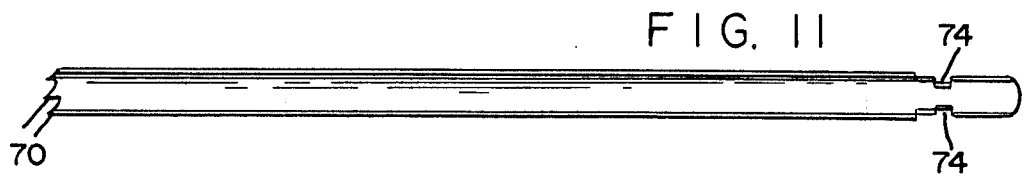
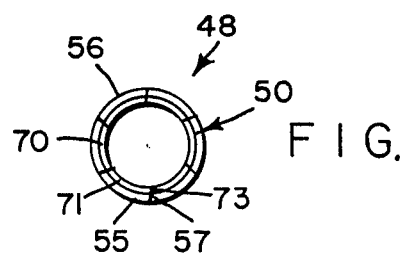

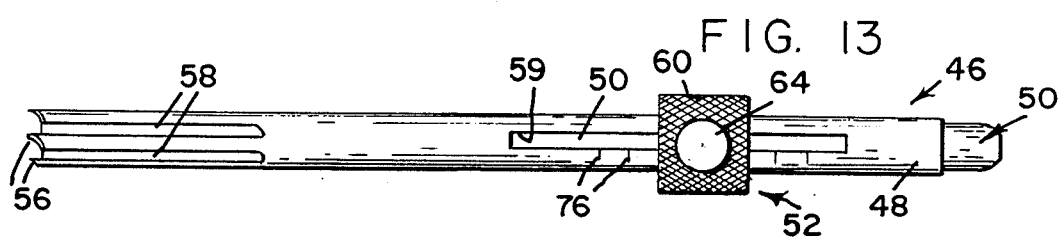
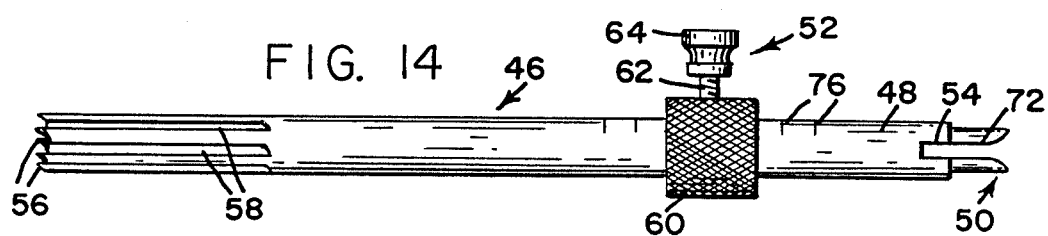
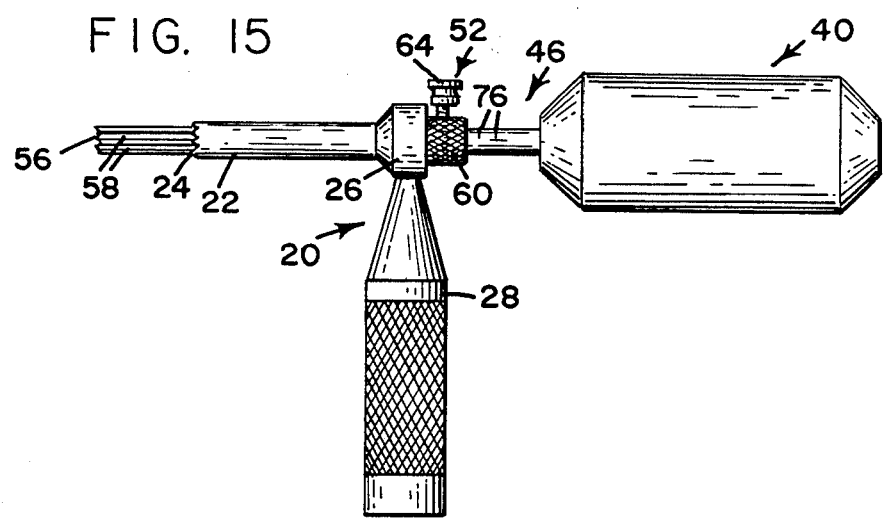
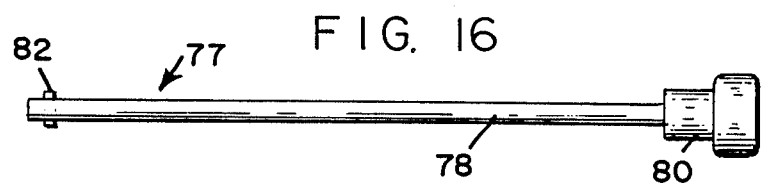

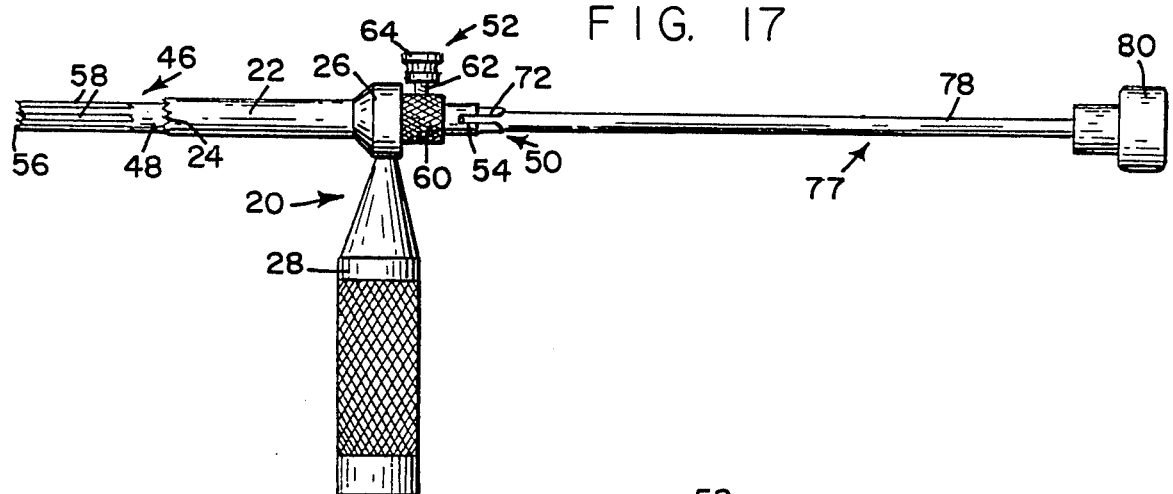
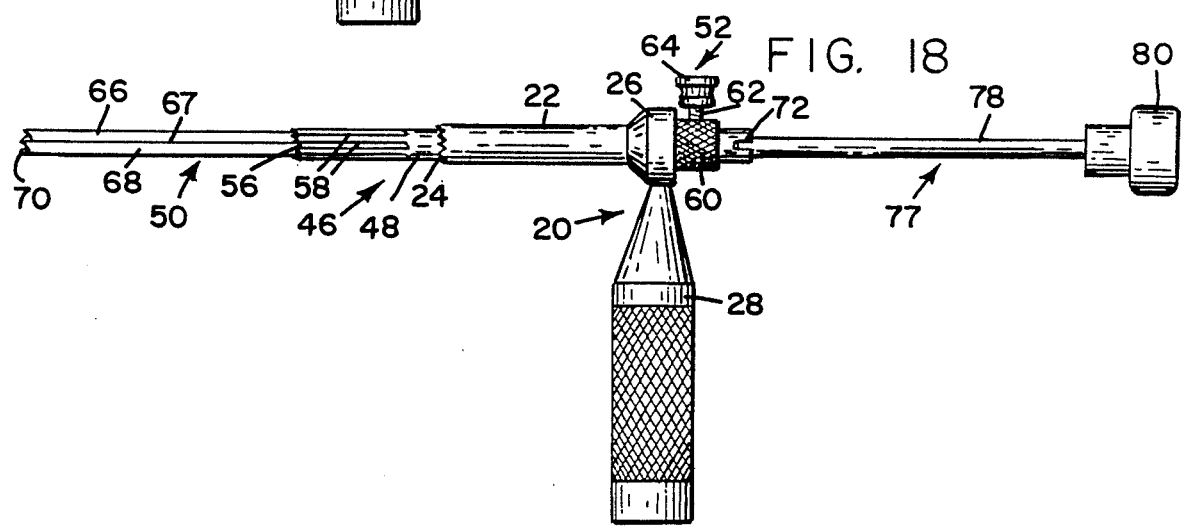
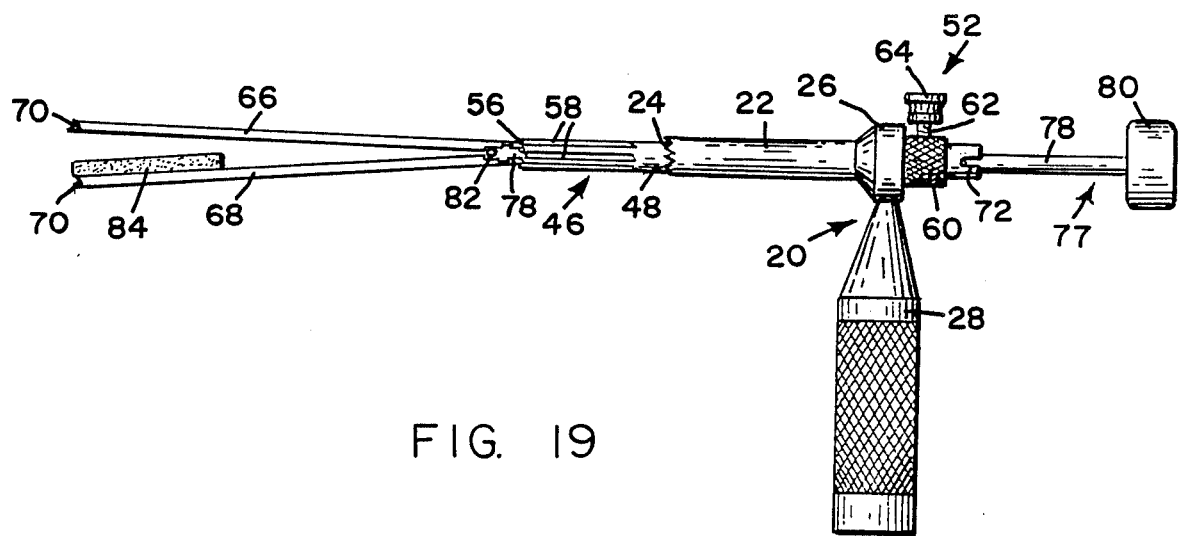

4,798,213

BONE BIOPSY APPARATUS

BACKGROUND OF THE INVENTION

The present invention is directed to an apparatus for obtaining a bone biopsy for diagnosis of various bone diseases. Qualitative histomorphometry of transiliac bone biopsies is a routine part of the assessment of patients with metabolic neoplastic infections and other disease processes. The diagnostic value of bone biopsy specimens depends on the expertise of the examiner and the quality of the specimen. The quality of the specimen, in turn, depends a great deal of the quality of the apparatus which is used for obtaining the bone biopsy specimen.

The bone biopsy apparatus which is currently being used comprises an introducer, a trocar, a cutting drill, and a plunger. The introducer includes a tube with gripping teeth on one end to grip against the outer surface of the bone from which a biopsy is to be taken. The trocar is a long pointed rod which extends through the tube of the introducer to penetrate skin and separate muscle tissue, and to locate the introducer on the bone surface. The drill is an elongated tubular member which has a turning handle at one end and cutting teeth at the other end. The drill is rotated about its longitudinal axis which causes the drill to cut into the bone. A bone core sample or specimen is formed within the tubular drill as it advances into the bone. The drill is then removed from the bone with the bone specimen within the drill. The bone specimen is then removed from the drill by inserting the plunger through the drill from the end which is opposite the cutting teeth for the drill. The bone specimen is then pushed out of the drill through the cutting end of the drill and collected for examination.

One of the major disadvantages of the present day bone biopsy apparatus is that the step of pushing the bone biopsy specimen out of the drill tends to damage the specimen. This seriously affects the quality of the biopsy and the diagnosis. Another disadvantaged of the bone biopsy apparatus which is currently being used is the presence of bone dust and bone debris in the bone sample or specimen. The dust and debris are created during drilling into the bone. The presence of this dust and debris affects the quality of the bone sample for diagnosis. Another problem which is encountered with the present day biopsy devices is that there is no way of determining how far the drill has penetrated into the bone. The drilling step of the biopsy is, therefore, very difficult. Also, it is not possible to obtain a core sample of a specific predetermined length. These and other difficulties experienced with the prior art bone biopsy devices have been obviated by the present invention.

It is, therefore, a principal object of the present invention to provide a bone biopsy apparatus which allows a bone biopsy specimen to be removed from the drill portion of the apparatus without any pressure being applied to the specimen to prevent the specimen from being damaged.

Another object of this invention is the provision of a bone biopsy apparatus which prevents bone dust and bone debris, which results from drilling into the bone, from being accumulated in the bone sample or specimen.

A further object of the present invention is the provision of a bone biopsy apparatus in which the depth of cut into the bone and the size of resulting bone specimen can be determined precisely.

It is another object of the present invention to provide a bone biopsy apparatus in which some of the elements of the apparatus are interchangeable. This results in the savings in cost and provides a more compact bone biopsy kit or package.

A still further object of the invention is the provision of a bone biopsy apparatus which is easy to use and is considerably safer than prior art biopsy devices.

It is a further object of the invention to provide a bone biopsy apparatus which is simple in construction and which is capable of a long life of useful service.

With these and other objects in view, as will be apparent to those skilled in the art, the invention resides in the combination of parts set forth in the specification and covered by the claims appended hereto.

SUMMARY OF THE INVENTION

In general, the invention consists of bone biopsy apparatus having an introducer which includes a guide tube, one end of which has a plurality of gripping teeth for maintaining the guide tube in position against the surface of the bone. A cylindrical tubular drill having cutting teeth at one end is mounted within the guide tube of the introducer for sliding movement along the longitudinal axis of the tube toward the bone for drilling into the bone and obtaining a bone sample. An adjustable stop is mounted on the drill for limiting the axial movement of the drill into the bone and thereby limiting the distance which the cutting teeth of the drill extend beyond the holding teeth of the introducer and into the bone. More specifically, the drill comprises an outer cylindrical retaining sheath and an inner cylindrical retaining sheath which is slidably mounted longitudinally within the outer retaining sheath. The inner retaining sheath consists of two separable longitudinal halves. The inner and outer retaining sheaths are held together as a single unit by releasable clamping means. Means are provided for removing the inner retaining sheath from the outer retaining sheath upon release of the clamping means. When the inner sheath is removed from the outer sheath, the two halves of the inner retaining sheath are separated to permit removable of a bone sample from within the inner retaining sheath, thereby preventing damage to the bone sample.

BRIEF DESCRIPTION OF THE DRAWINGS

The character of the invention, however, may be best understood by reference to one of its structural forms, as illustrated by the accompanying drawings, in which:

FIG. 8 is a side elevational view of an outer retaining sheath which forms part of the drill portion of the present invention, FIG. 9 is a side elevational view of an inner retaining sheath which also forms part of the drill portion of the present invention, FIG. 10 is a top plan view of the top half of the inner retaining sheath, FIG. 11 is a bottom plan view of the top half of the inner retaining sheath, FIG. 12 is a front elevational view of the drill portion of the present invention, FIG. 13 is a plan view of the inner and outer retaining sheaths combined to form the drill portion of the present invention, FIG. 14 is a side elevational view of the drill, FIG. 15 is a side elevational view of the drill shown in operating position within the introducer portion of the present invention and showing the handle portion of the present invention attached to the rear end of the drill, FIG. 16 is a plan view of the extractor portion of the present invention for removing the inner retaining sheath from the outer retaining sheath, and FIGS. 17–19 are operational views which illustrate the steps for removing a bone sample from within the inner retaining sheath.

DESCRIPTION OF THE PREFERRED EMBODIMENT

Figure 1:
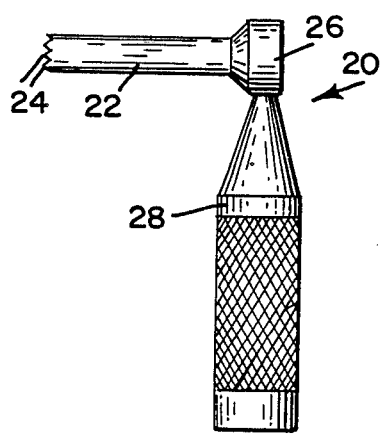
FIG. 1 is a right side elevational view of the introducer portion of the present invention.
Figure 2:
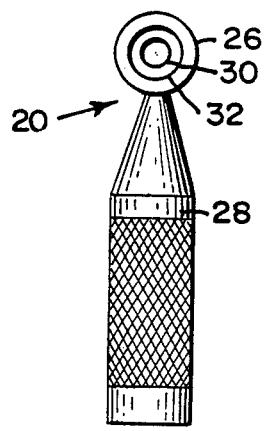
FIG. 2 is a rear elevational view of the introducer.
Figure 6:
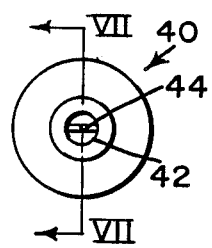
FIG. 6 is a front elevational view of the handle shown in FIG. 5.
Figure 4:
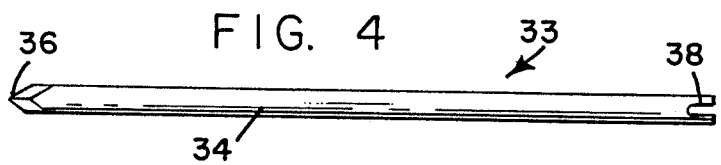
FIG. 4 is a side elevational view of the trocar portion of the present invention.
Figure 3:
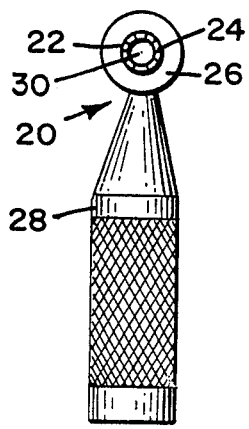
FIG. 3 is a front elevational view of the introducer.
Figure 7:
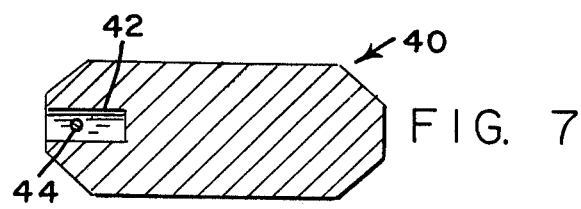
FIG. 7 is a vertical cross-sectional view of the handle taken along the line VII-VII of FIG. 6 and looking in the direction of the arrows.

Referring first to FIGS. 1, 2, and 3, the introducer portion of the present invention is generally indicated by the reference numeral 20 and comprises an elongated tube 22 and a handle 28 which extends at a right angle to the central longitudinal axis of the tube 22. The tube 22 is open at both ends. The front end of the tube 22 has a plurality of sharp holding teeth 24 while the rear end of the tube has an enlarged head portion 26. The bore of the tube 22 is indicated by the reference numeral 30 in FIG. 2 and is coaxial with a counterbore 32 in the head portion 26. The enlarged head 26 enables the introducer to be tapped with a mallet to set the teeth 24 into the bone. The counterbore 32 ensures that only the outer portion of the head 26 is struck by the mallet to prevent deformation at the end of the bore 30 and thereby prevent eventual occlusion of the bore. The upper end of the handle 28 has a threaded projection, not shown, which is threaded into an appropriate threaded aperture, not shown, in the head 26. This enables the handle 28 to be removed from the tube 22 for compact storage of the introducer during periods of nonuse.

Figure 5:
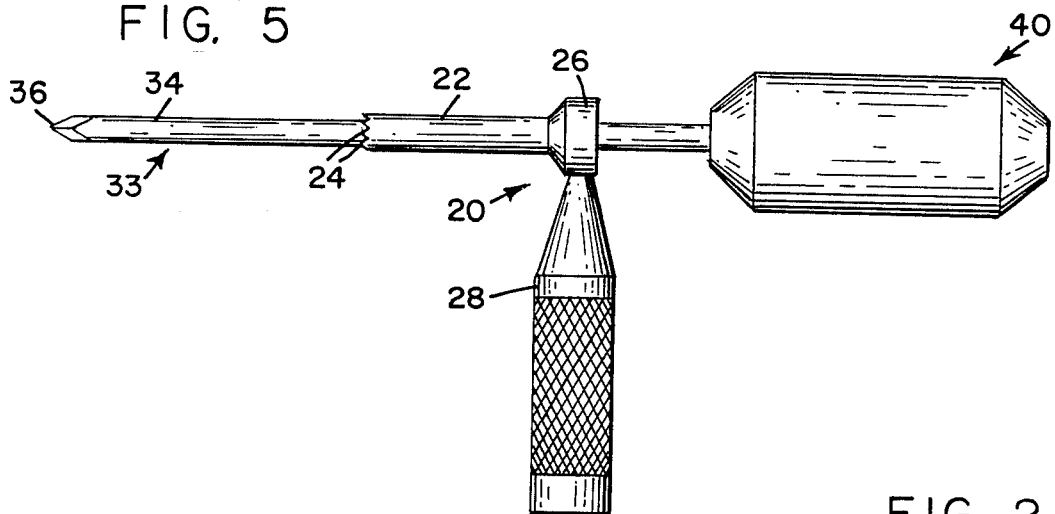
FIG. 5 is a side elevational view of the trocar of FIG. 4 in operating position within the introducer, the operating handle of the present invention also being shown attached to the trocar.

Referring to FIGS. 4–7, the trocar portion of the present invention is generally indicated by the reference numeral 33 and comprises an elongated rod 34 which has a pointed front end 36 and a notch 38 at the rear end of the rod. The trocar also includes a removable handle which is generally indicated by the reference numeral 40. The front end of the handle 40 has a cavity 42 and a drive pin 44 which extends through the cavity 42. The handle 40 is applied to the rear end of the rod 34 by inserting the rear end of the rod into the cavity 42 so that the pin 44 enters the notch 38. The trocar 33 is applied to the introducer 20 by inserting the pointed front end 36 through the bore 30 from the enlarged head 26 so that the pointed front end 36 extends forwardly of the gripping teeth 24 as shown in FIG. 5.

The sharp end 36 of the trocar enables the trocar to penetrate soft tissue and to act as a guide for locating the tubular portion 22 of the introducer against the surface of the bone which is to be biopsied. The outer surface of the handle 28 is preferably knurled for better gripping. The placement of the handle 28 at a substantial angle to the axis of the tube 22 makes the introducer easier to grip and allows for accurate placement of the trocar at the beginning of a bone biopsy sequence.

Referring to FIGS. 13 and 14, the drill portion of the present invention is generally indicated by the reference numeral 46 and comprises an outer retaining sheath 48 and an inner retaining sheath which is generally indicated by the reference numeral 50. Referring also to FIG. 8, the outer retaining sheath 48 is open at both ends. The forward end of the outer retaining sheath has a plurality of cutting teeth 56 and the rear end of the sheath has a pair of diagonally opposed notches 54. A plurality of grooves 58 extend rearwardly from the teeth 56 for approximately the first forward quarter of the outer retaining sheath. There is one groove 58 for each tooth 56. The drill 46 also includes a clamping device which is generally indicated by the reference numeral 52 which comprises a collar 60 which is slidably mounted on the outer surface of the outer retaining sheath 48. The clamp 52 also includes a set screw 62 which has an enlarged head 64 which allows the set screw to be turned by hand. The set screw 62 is threaded into an aperture, not shown, in the collar 60 which extends entirely through the collar.

Referring also to FIGS. 9–11, the inner retaining sheath 50 comprises two half portions 66 and 68 which are separable along a longitudinal parting line 67. Both ends of the inner retaining sheath 50 are open. The forward end of the inner retaining sheath is provided with a plurality of cutting teeth 70 and the rear end of the sheath is provided with a pair of diagonally opposed longitudinal notches 72. Each notch 72 has a pair of opposed lateral notches 74 for a purpose to be described. The inner retaining sheath 50 is slidably mounted within the outer retaining sheath 48 as shown in FIGS. 13 and 14. The teeth 70 of the inner sheath 50 are complimentary with the cutting teeth 56 of the outer sheath 48 so that when the inner sheath is properly aligned within the outer sheath, the teeth 70 combine with the teeth 56 to form a single set of teeth as shown in FIG. 12. The teeth 70 and 56 are properly aligned when the teeth 70 and 56 are at the same forward point along the central longitudinal axis of the drill, and when the notches 54 and 72 are in alignment about the axis. This alignment is accomplished by an extractor which is generally indicated by the reference numeral 77 in FIG. 16. The extractor 77 comprises an elongated rod 78 which has a handle 80 at its rearward end and an alignment pin 82 at its forward end. The inner retaining sheath 50 is aligned about the central longitudinal axis of the drill within the outer retaining sheath 48 by inserting the extractor 77 within the inner retaining sheath 50 so that the alignment pin 82 extends into the notches 72. Axial rotation of the extractor 77 causes the inner retaining sheath 50 to be rotated axially relative to the outer retaining sheath 48 so that the notch 72 of the inner retaining sheath is aligned with the notch 54 of the outer retaining sheath. Positioning of the inner retaining sheath relative to the outer retaining sheath along the central longitudinal axis of the drill is accomplished by positioning the alignment pin 82 so that it is aligned with the lateral notches 74. The extractor 77 is rotated slightly about its central longitudinal axis until one end of the pin engages one of the lateral notches 74 on one side of one half portion of the inner retaining sheath 50 and the opposite end of the pin engages one of the lateral notches 74 on the opposite side of the other half of the inner retaining sheath. This enables the inner retaining sheath 50 to be moved forwardly and rearwardly by the extractor 77 along the central longitudinal axis of the drill for aligning the teeth 70 with the teeth 56 so that they are at the same forward position. Alignment of the teeth about the central longitudinal axis of the drill is thereafter accomplished by rotating the extractor 77 about its central longitudinal axis so that the notches 54 and 72 are aligned as shown in FIG. 14. When the inner and outer retaining sheaths 50 and 48, respectively, are properly aligned, the collar 60 is positioned so that the set screw 62 is aligned with the elongated slot 59. Tightening of the screw 62 causes the end of the screw to pass through the slot 5 and engage the outer surface of the inner retaining sheath 50. This clamps the inner and outer retaining sheaths firmly together so that they function as a single drill unit.

Referring particularly to FIG. 12, each cutting tooth 56 has a pair of outwardly facing facets 55 and 57. Each tooth 70 also has a pair of outwardly facing facets 71 and 73 which are complimentary with the facets 55 and 57, respectively. When the teeth 56 and 70 are aligned, the facets 71 and 73 are extensions of the facets 55 and 57, respectively. There is a groove 58 for each cutting tooth 56 and each groove extends from a point where the facet 55 of one tooth meets the facets 57 of the adjacent tooth. This ensures that bone dust and bone debris which is formed during drilling of a bone sample is guided into the grooves 58 by the teeth for rearward migration along the grooves. The dust and debris is thereby prevented from entering into the drill and contaminating the bone sample as it is being formed.

Referring to FIG. 15, the drill 46 is coupled with the introducer 20 by inserting the forward end of the drill through the enlarged head portion of 26 so that the forward end of the drill extends beyond the teeth 24 of the tube 22. The amount that the drill 46 extends beyond the forward end of the tube 22 is determined by the position of the clamping means 52 on the outer retaining sheath 48. The slot 59 enables the clamp 52 to be positioned along the outer retaining sheath at a plurality axial positions along the central longitudinal axis of the drill while, at the same time, enables the clamp to retain its function of clamping the inner and outer sheaths together. The length of the bone core sample to be taken for biopsy is determined by the distance that the forward end of the drill extends beyond the forward end of the tube 22. The outer surface of the outer retaining sheath 48 is provided with a plurality of marks 76 which enable the clamp 52 to be located at a plurality of predetermined set positions which corresponds to a plurality of predetermined bone biopsy sample lengths. The handle 40 is applied to the drill 46 by inserting the rear end of the drill into the cavity 42 so that the pin 44 enters into the notches 54 and 72. This enables the drill to be rotated axially by rotating the handle 40 axially.

The operation and advantages of the present invention will now be readily understood in view of the above description. The initial step for obtaining a bone sample as part of a bone biopsy is combining of the trocar 33 with the introducer 20. The rod 34 is inserted through the tube 22 so that the pointed forward end 36 of the rod extends forwardly of the forward end of the tube 22 as shown in FIG. 5. The handle 40 is thereafter applied to the rear end of the rod 34. When the pointed end 36 is properly positioned against the patient's skin in alignment with the bone to be biopsied, the trocar is pushed through the patients soft tissue by pushing on the handle 40 until the pointed end 36 comes to rest against the bone. The tube 22 of the introducer 20 is guided along the rod 34 until the teeth 24 also come to rest against the bone which is to be biopsied. The trocar is then removed from the patient and the head 26 of the introducer is struck by a mallet to set the teeth 24 of the tube 22 firmly against the outer surface of the bone. At this point, the assembled drill 46 is coupled with the introducer 20 by inserting the forward end of the drill into the tube 22 from the head 26 so that the forward end of the drill also comes to rest against the surface of the bone. The handle 40 is then applied to the rear end of the drill 46 as shown in FIG. 15. The drill is advanced into the bone by rotating the handle 40 about its central longitudinal axis until the collar 60 strikes the head 26. When this occurs, the forward end of the drill has penetrated into the bone a predetermined distance and has obtained a bone sample of a predetermined length. The bone sample is broken off from the bone by wriggling the introducer In the case of a relatively small bone, it may be preferred to set the drill relative to the introducer so that the drill passes entirely through the bone but not beyond the outer surface of the bone. The bone sample thus obtained will be equal to the thickness of the bone which is biopsied. Once that the bone sample has been secured by the drill, the drill is removed from the patient.

Referring particularly to FIGS. 17-19, the bone sample is removed from the drill 46 by removing the handle 40 and attaching the forward end of the extractor 77 to the rearward end of the drill 46 as shown in FIG. 17. The forward end of the extractor 77 is inserted into the drill so that the alignment pin 82 enters the notches 72 and 54. The set screw 62 is loosened to enable the inner retaining sheath 50 to be moved axially relative to the outer retaining sheath 48. The length of the alignment pin 82 is less than the inner diameter of the outer retaining sheath 48 but is greater than the inner diameter of the inner retaining sheath 50. This means that the forward end of the extractor 77 can move freely within the outer retaining sheath 48 but will engage the rear end of the inner retaining sheath 50. The forward end of the extractor 77 is inserted into the notches 72 and 54 so that the pin 82 engages the end of the inner retaining sheath 50. As the extractor 77 is pushed forwardly as shown in FIG. 18, the inner retaining sheath 50 is pushed forwardly out of the outer retaining sheath 48. The inner retaining sheath 50 can be pushed entirely through the outer retaining sheath 48. This enables the halves 66 and 68 of the inner sheath to be separated for removal of an undamaged bone sample which is indicated by the reference numeral 84 in FIG. 19.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

I claim:

1. A drill for bone biopsy comprising:
   (a) an outer cylindrical retaining sheath having a first open end and a second open end with cutting teeth, (b) an inner cylindrical retaining sheath which is slidably mounted longitudinally within said outer retaining sheath, said inner retaining sheath having a first end and a second open end with cutting teeth, said inner retaining sheath comprising two separable longitudinal halves, (c) clamping means for releasably locking said inner and outer retaining sheaths together as a single drilling unit, (d) means for rotating said drill about its central longitudinal axis, and (e) means for removing said inner retaining sheath through the second open end of the outer retaining sheath.

2. A drill as recited in claim 1, wherein each tooth of said cutting teeth of said inner and outer retaining sheaths has at least two facets and the facets of each tooth face outwardly.

3. A drill as recited in claim 2, wherein the cutting teeth of said inner retaining sheath are complementary with the cutting teeth of said outer retaining sheath so that for at least one predetermined position of said inner retaining sheath relative to said outer retaining sheath the cutting teeth of said inner retaining sheath are aligned with the cutting teeth of said outer retaining sheath to form a single set of cutting teeth.

4. A drill as recited in claim 3, wherein said inner and outer retaining sheaths are provided with complementary indicator means for aligning said inner retaining sheath relative to said outer retaining sheath in said predetermined position.

5. A drill as recited in claim 4, wherein said outer retaining sheath has an outer surface which is provided with a plurality of longitudinal grooves which extend from said cutting teeth toward the first end of said outer retaining sheath.

6. A drill as recited in claim 5, wherein each tooth of said outer retaining sheath has first and second facets and the first facet of one tooth intersects with the second facet of the adjacent tooth, and wherein one of said grooves extends from each intersection of said first and second facets.

7. A drill as recited in claim 4, wherein said indicator means comprises a notch in the first end of each of said inner and outer retaining sheaths.

8. A drill as recited in claim 7, wherein the means for rotating said drill comprises a handle which is removably mounted on the end of the drill which has said complementary notches, said handle having a drive pin at one end of the handle which extends transversely of the central longitudinal axis of the drill for insertion into said complementary notches when the notches are in alignment for rotating said drill about said axis.

9. A drill as recited in claim 8, wherein said set screw has an enlarged head which extends beyond said collar for tightening and releasing said set screw by hand.

10. A drill as recited in claim 8, wherein said opening is an elongated longitudinal slot which enables said collar to occupy a plurality of clamping positions along said slot.

11. A drill as recited in claim 7, wherein the means for removing the inner retaining sheath from said outer retaining sheath is an elongated extractor which has a handle at one end and an engaging element at its opposite end for engaging the first end of said inner retaining sheath and for longitudinal sliding movement within said outer retaining sheath.

12. A drill as recited in claim 11, wherein the opposite end of said extractor has a transverse pin for engaging the notch in the first end of said inner retaining sheath.

13. A drill as recited in claim 1, wherein said clamping means comprises:
(a) a slot in said outer retaining sheath,
(b) a collar which is mounted for longitudinal sliding movement on said outer retaining sheath, said collar having a threaded aperture which extends completely through said collar transversely of said slot, and
(c) a set screw which is threaded in said aperture for extending through said opening for engaging said inner retaining sheath.

14. A drilling device for obtaining a bone biopsy comprising:
(a) an introducer comprising an elongated cylindrical guide tube which has a central longitudinal axis, said guide having a first open end and a second open end which has a plurality of gripping teeth for maintaining the guide tube in position against the outer surface of the bone,
(b) a handle which is attached to the guide tube for holding the introducer during drilling,
(c) a cylindrical tubular drill which is inserted within said guide tube for sliding movement along said longitudinal axis relative to said guide tube, said drill having a first end and a second open end which has a plurality of cutting teeth which extend beyond said gripping teeth upon insertion of said drill through said tube, said drill comprising:
(1) an outer cylindrical retaining sheath having a first open end and a second open end which is provided with cutting teeth,
(2) an inner cylindrical retaining sheath which is slidably mounted longitudinally within said outer retaining sheath, said inner retaining sheath having a first end and a second open end which is provided with cutting teeth, said inner retaining sheath comprising two separable longitudinal halves, and
(3) clamping means for releasably locking said inner and outer retaining sheaths together as a. single drilling unit,
(d) an adjustable stop which is mounted on said drill for limiting the axial movement of said drill toward the second end of said introducer and thereby limiting the distance which the cutting teeth of the drill extend beyond the holding teeth of the introducer,
(e) means for rotating said drill about its central longitudinal axis, and
(f) means for removing a bone biopsy sample form said drill including means for removing said inner retaining sheath through the second open end of the outer retaining sheath.

15. A drilling device as recited in claim 14, wherein said adjustable stop comprises:
(a) a collar which is mounted for longitudinal sliding the first end of said introducer, said collar having a threaded aperture which extends completely through said collar transversely of said central longitudinal axis, and
(b) a set screw which is threaded into said aperture for engaging said drill.

16. A drilling device as recited in claim 15, wherein said clamping means comprises, in part, of said adjustable stop, and an elongated longitudinal slot in said outer retaining sheath which enables said set screw to engage said inner retaining sheath for clamping said inner and outer retaining sheaths together and allowing said collar to be moved to a plurality of positions along the length of said slot.

17. A drill as recited in claim 16, wherein said set screw has an enlarged head which extends beyond said collar for tightening and releasing said set screw by hand.

18. A drilling device as recited in claim 14, wherein the means for removing said inner retaining sheath from said outer retaining sheath comprises:

(a) a notch in the first end of said inner retaining sheath, and (b) an elongated extractor having a handle at one end and an engaging element at its opposite end for engaging said notch and for longitudinal sliding movement within said outer retaining sheath.

19. A drilling device as recited in claim 18, wherein the means for rotating said drill comprises a turning handle which has a drive pin at one end for engaging said notch.

20. A drilling device as recited in claim 19, wherein said turning handle has a cavity at said one end for receiving the first ends of said inner and outer retaining sheaths and wherein said drive pin extends transversely through said cavity.

* * * * *